US00PP10120P

United States Patent [19]

Nagase

[11] Patent Number: Plant 10,120

[45] Date of Patent: Nov. 18, 1997

[54] TORENIA PLANT 'SUNRENIMU'

[75] Inventor: Yuki Nagase, Seki, Japan

[73] Assignee: Suntory Limited, Osaka, Japan

[21] Appl. No.: 559,840

[22] Filed: Nov. 20, 1995

[51] Int. Cl.[6] ..... A01H 5/00

[52] U.S. Cl. ..... Plt./68.1

[58] Field of Search ..... Plt./68.1

*Primary Examiner*—James R. Feyrer

*Attorney, Agent, or Firm*—Morgan & Finnegan; Eugene Moroz; Mary J. Morry

[57] ABSTRACT

A new and attractive hybrid of Torenia plant, names 'Sunrenimu', attained from 'Crown Violet'×'Con Color'. The new plant has a less decumbent, more ascending or semi-upright habit and a more open canopy. This plant produces a profusion of flowers of purple with a lighter purple corolla tube coloration; and has a high resistance to heat, moderate resistance to pests and diseases and is shade tolerant to produce copious flowers from about late June to October, or until killed by frost.

3 Drawing Sheets

BACKGROUND OF THE VARIETY

The present invention relates to a new and distinct variety of torenia plant obtained from crossing "Crown Violet" (♀) and "Con Color" (♂).

The torenia is a very popular plant and is used for flower bedding and potting in the summer season. There are only a few varieties of the torenia plant which have a semi-erect growth habit, a high resistance to heat and diseases. And the torenia plant needs full sunshine and hardly grows and has flowers in the shade of trees. Accordingly, this invention was aimed at obtaining a new variety having a great profusion of flowers, dark reddish purple flower petal with light purple floral tube, semi-erect growth habit, a high resistance to heat and diseases, and growing and having flowers ordinarily in the shade of trees.

The new variety of torenia plant according to this invention originated from crossing "Con Color" as pollen parent and "Crown Violet" as female parent. This new variety is an interspecific hybrid from within the genus Torenia.

From the initial cross noted above, a total hybrid population of 25 plants was obtained from seeds of the cross. These plants were started in February 1993, and cultured in the Plant Biotechnology Laboratory, Institute for Fundamental Research of SUNTORY Ltd., located at 101, Wakayamadai 1-chrom, Shimamoto-cho, Mishima-gun, Osaka-fu, Japan. Plantlets were sprouted and allowed to grow to transplant stage. The siblings of the population were then individually placed in pots on benches, and later placed in beds, for initial trials during the summer of 1993. The population was grown to maturity to allow for the observation of the plants for their individual traits, and to allow for comparison of the individuals with the parents. One individual conspicuously differed from the remainder of the siblings by having a more desirable growth habit, desirable flower counts and characteristics, and was selected for further tests and observation. Upon closer examination, it has been concluded that this plant is distinguishable from all other varieties of Torenia known to us. The selected plant was then asexually reproduced, by the taking and rooting of cuttings at the location noted above. Clonal progeny from such cuttings were observed to be uniform and stable, and have been identical to the initial selection in all distinguishing characteristics. Based on the selection and testing of this plant, it was determined that this plant not only had highly desirable growth and blooming habits and flower characteristics, but had an unusually high tolerance of heat and shaded conditions. It has been named 'Sunrenimu'.

In the following description, the color-coding is in accordance with The Horticultural Colour Chart of The Royal Horticultural Society , London, England (R.H.S. Colour Chart), and the Inter-Society color Council-Nation Bureau of Standard Color Name (I.S.C.C.-N.B.S. Color Name). A color chart based on The Japan Color Standard for Horticultural Plant (J.H.S. Color Chart) is also added for reference.

The female parent used in the crossing of this new variety "Sunrenimu" was "Crown Violet", one of the Crown Series bred by the Sakata Seed Corp., Japan. The Crown Series includes plant having white petal, purplish blue flower petals, bi-color of white and purplish blue and the like, and these plants are commonly characterized by a high resistance to heat and are on the market in Japan. The main botanical characteristics of "Crown Violet" are as follows.

Plant:
- *Growth habit.*—Erect.
- *Plant height.*—20–30 cm.
- *Plant extension.*—30–50 cm.

Stem:
- *Diameter.*—3.0 mm.
- *Anthocyanin pigmentation.*—Present.
- *Branching.*—Few.
- *Pubescence.*—Few.
- *Length of internode.*—1–3 cm.

Leaf:
- *Phyllotoxis.*—Opposite.
- *Shape of blade.*—Serrate.
- *Length.*—2.0–4.0 cm.
- *Width.*—2.0–3.0 cm.
- *Depth of incision.*—Deep.
- *Color.*—Moderate olive green (R.H.S. 137A, JHS 3508)
- *Pubescence.*—Few.

Flower:
- *Facing direction.*—Laterally.
- *Diameter.*—2.0–3.0 cm.
- *Height.*—20–30 mm.
- *Color of floral tube.*—Soft violet (R.H.S. 92C, JHS 8008).
- *Color of petal.*—Single color; purplish white (R.H.S. 62D, JHS 8001).
- *Yellow eye color.*—Present. Vivid yellow (R.H.S. 17C, JHS 2507).

*Calyx.*—1.5–2.0 cm in length.
*Anthocyanin pigmentation of calyx limb. — Present.*
*Peduncle.*—1.5–2.0 mm in thickness; and 1.5–2.0 cm in length.
*Reproductive organs.*—1 pistil and 4 stamens.
*Anther color.*—White.
*Flowering duration.*—Medium.

Physiological and ecological characteristics: Low resistance to diseases and pests, high tolerances to heat and low tolerance to cold.

"Con Color", used as the male parent in the crossing of this new variety "Sunrenium", is one of the Con Color Series bred by the Sakata Seed Corp., Japan. The Con Color Series includes plant having violet flower petal, bi-color of storing purple and Pale purple and the like, and these plants are commonly characterized by a high resistance to heat and are on the market in Japan. The main botanical characteristics of "Con Color" are as follows.

Plant:
*Growth habit.*—Decumbent.
*Plant height.*—10–15 cm.
*Plant extension.*—50–70 cm.

Stem:
*Diameter.*—1.5 mm.
*Anthocyanin pigmentation.*—Present.
*Branching.*—Many.
*Pubescence.*—Few.
*Length of internode.*—4–6 cm.

Leaf:
*Phyllotaxis.*—Opposite.
*Shape of blade.*—Crenate.
*Length.*—1.0–2.0 cm.
*Width.*—1.0–2.0 cm.
*Depth of incision.*—Medium.
*Color.*—Moderate olive green (R.H.S. 137A, JHS 3508)
*Pubescence.*—Few.

Flower:
*Facing direction.*—Laterally.
*Diameter.*—2.0–3.0 cm.
*Height.*—20–30 mm.
*Color of floral tube.*—Moderate Purple (R.H.S. 83B, JHS 8613).
*Color of petal.*—Single color; deep purple (R.H.S. 89C, JHS 8311).
*Yellow eye color.*—Absent.
*Calyx.*—1.5–2.0 cm in length.
*Anthocyanin pigmentation of calyx limb.*—Present.
*Peduncle.*—1.5–2.0 mm in thickness; and 3.0–5.0 cm in length.
*Reproductive organs.*—1 pistil and 4 stamens.
*Anther color.*—White.
*Flowering duration.*—Medium.

Physiological and ecological characteristics: High resistance to diseases and pests, high tolerances to heat and low tolerance of cold.

SUMMARY OF THE VARIETY

The new variety of torenia plant has a semi-erect habit, dark reddish purple flower petal with light purple floral tube without yellow eye color, and thus is very different from a similar variety, "Crown Violet" and "Con Color". The plant has a semi-erect habit, medium branching and great profusion blooms, and the whole bush remains in bloom for a considerable period of time. The plant has a high resistance to heat, moderate resistance to diseases and pests, and grows and has flowers ordinarily in the shade of trees.

DESCRIPTION OF THE VARIETY

Figure 1:
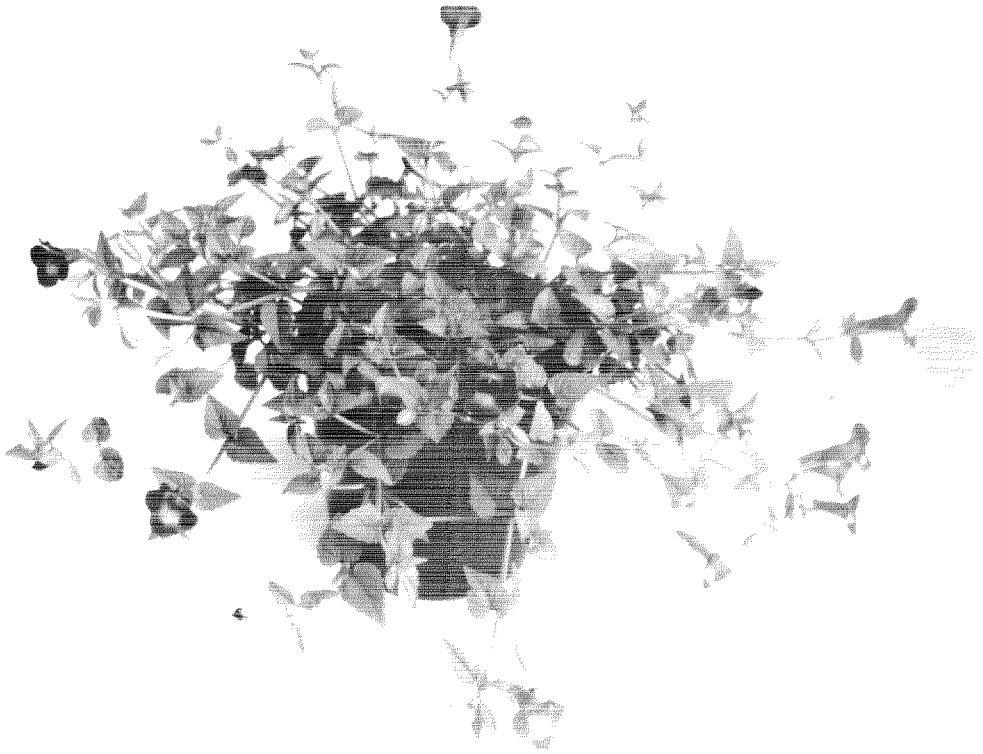
FIG. 1 is a photograph giving a partial view of the new variety of torenia plant planted in a flower pot.
Figure 2:
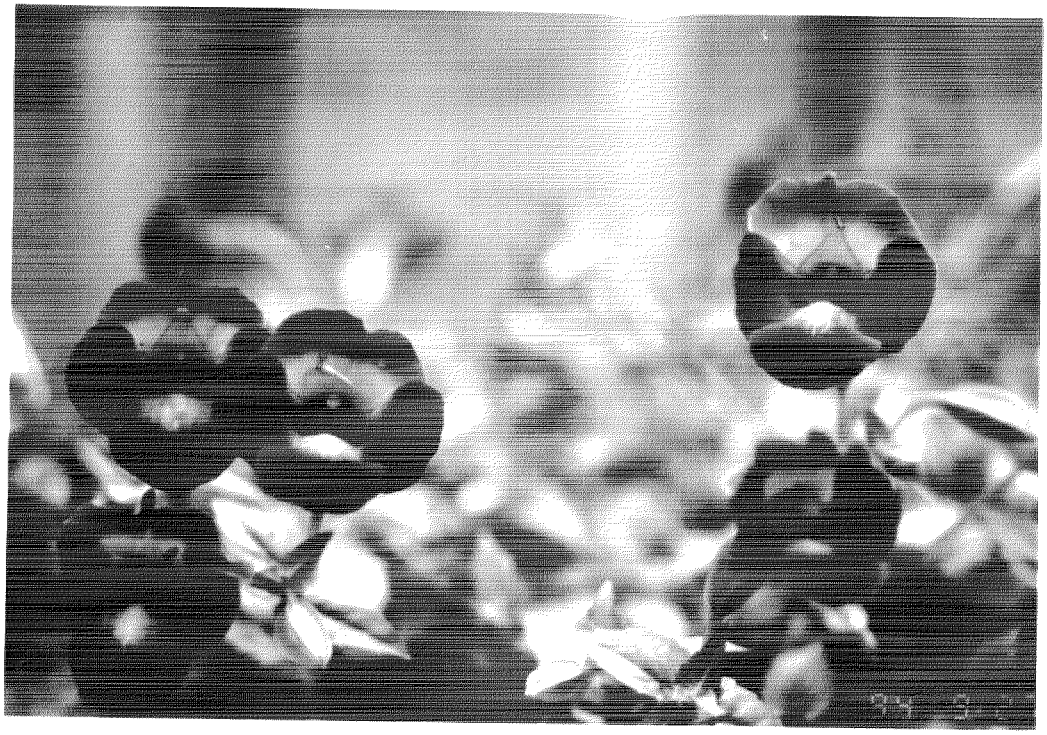
FIG. 2 is a photograph of flowers of the new variety of torenia plant.
Figure 3:
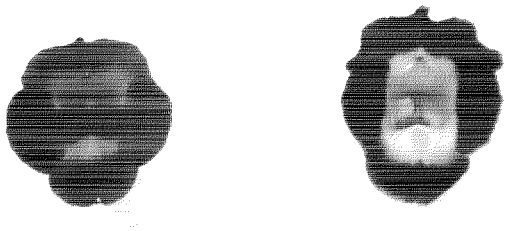
FIG. 3 is a photograph of the flowers of the new variety of torenia plant, Sunrenimu (on the left) and the Crown Violet variety (on the right).

The botanical characteristics of the new and distinct variety of torenia plant "Sunrenimu" are as follows.

Plant:
*Growth habit.*—Semi-erect. The stems hang down pliantly when potted in a hanging pot.
*Plant height.*—10–20 cm.
*Plant extension.*—50–60 cm. The stem extends to length of 60 cm from the base.
*Growth.*—Medium branching, a great profusion of blooms; the whole bush remaining in bloom for a considerable period of time.
*Blooming period.*—June to November in the the southern Kanto area, Japan. The plant shape does not change throughout this period.

Stem:
*Diameter.*—2.0 mm.
*Anthocyanin pigmentation.*—Present.
*Branching.*—Medium.
*Pubescense.*—Few.
*Length of internode.*—6–8 cm.

Leaf:
*Phyllotaxis.*—Opposite.
*Shape of blade.*—Serrate.
*Length.*—2.0–3.0 cm.
*Width.*—1.5–2.5 cm.
*Depth of incision.*—Medium.
*Color.*—Moderate olive green (R.H.S. 137A, JHS 3508)
*Pubescence.*—Few.

Flower:
*Facing direction.*—Laterally.
*Diameter.*—2.0–3.0 cm.
*Height.*—30–40 mm.
*Color of floral tube.*—Light Purple (R.H.S. 92B, JHS 8303).
*Color of petal.*—Single color; dark reddish purple (R.H.S. 83B, JHS 8909).
*Yellow eye color.*—Absent.
*Calyx.*—1.5–2.0 cm in length.
*Anthocyanin pigmentation of calyx limb.*—Present.
*Peduncle.*—1.5–2.0 mm in thickness; and 2.0–3.0 cm in length.
*Reproductive organs.*—1 pistil and 4 stamens.
*Anther color.*—White.
*Flowering duration.*—Medium.

Physiological and ecological characteristics: Medium resistance to diseases and pests, high tolerances to heat and low tolerance to cold. The plant grows and has flowers ordinarily in the shade of trees.

This new variety "Sunrenimu" of torenia plant is most suitable for flower bedding and potting, particularly in hanging pots or planters.

This new variety "Sunrenimu" was asexually reproduced by cutting.

The plant of this new variety "Sunrenimu" is presently planted and maintained at the Nursery Center of the Plant Biotechnology Laboratory, Institute for Fundamental Research of SUNTORY Ltd., residing at 2913-1 Torihara, Hakushu-cho, Kitakoma-gun, Yamanashi-ken, Japan and the Plant Biotechnology Laboratory, Institute for Fundamental Research of SUNTORY Ltd., residing at 1-1, Wakayamadai 1-chome, Shimamoto-cho, Mishima-gun, Osaka-fu, Japan.

I claim:

1. A new and distinct variety of the torentia plant characterized as to novelty by its semi-erect habit, dark reddish purple flower petal with light purple floral tube without yellow eye color, substantially as shown and described.

* * * * *

1/3

2/3

3/3